United States Patent [19]
Furubayashi et al.

[11] Patent Number: 4,515,653
[45] Date of Patent: May 7, 1985

[54] METHOD FOR PRODUCTION OF A MOISTURE SENSOR

[75] Inventors: Hisatoshi Furubayashi, Yamatokoriyama; Junichi Tanaka; Masanori Watanabe, both of Tenri; Masaya Hijikigawa, Yamatokoriyama, all of Japan

[73] Assignee: Sharp Kabushiki Kaisha, Osaka, Japan

[21] Appl. No.: 604,386

[22] Filed: Apr. 27, 1984

[30] Foreign Application Priority Data

Apr. 30, 1983 [JP] Japan .................................. 58-77807
May 7, 1983 [JP] Japan .................................. 58-79731

[51] Int. Cl.³ ........................ B44C 1/22; C03C 15/00; C03C 25/06; B29C 17/08
[52] U.S. Cl. ........................................ 156/643; 73/73; 156/646; 156/655; 156/659.1; 156/668; 156/902; 204/192 E; 236/44 R

[58] Field of Search ..................................... 73/73–77; 156/643, 646, 655, 659.1, 668, 901, 902; 236/44 R, 44 C, 44 E, DIG. 13; 204/192 E, 164; 252/79.1

[56] References Cited

U.S. PATENT DOCUMENTS 4,357,369 11/1982 Kilichowski et al. .......... 156/643 X

Primary Examiner—William A. Powell
Attorney, Agent, or Firm—Keil & Weinkauf

[57] ABSTRACT

A method for production of a moisture sensor comprising forming a moisture sensitive polymer film on a substrate, disposing a patterned masking material on said moisture sensitive polymer film, and etching said moisture sensitive film by means of an oxygen plasma, whereby a desired fine pattern of the moisture sensitive film is formed with fair accuracy and reproducibility.

6 Claims, 12 Drawing Figures

METHOD FOR PRODUCTION OF A MOISTURE SENSOR

BACKGROUND OF THE INVENTION

1. Field of the Invention

The present invention relates to a method for preparation of a moisture sensor, having a moisture sensitive film made of a polymer, which detects variation of humidity in the atmosphere by means of measurement of a variation in the impedance of the polymer film.

2. Description of the Prior Art

As a moisture sensor wherein an impedance varies depending upon a variation of humidity in the atmosphere, there have been, for example, a moisture sensor having a sintered body of metal oxides such as tin oxide ($SnO_2$), or a metal oxide film; a moisture sensor having a hydrophilic polymer film; a moisture sensor having an electrolyte salt such as lithium chloride (LiCl); and a moisture sensor having a hygroscopic resin or polymer film in which conductive particles or fibers such as carbon are dispersed.

While a moisture sensor containing a metal oxide film or a hydrophilic film has a wide moisture-sensitivity range, its resistance varies exponentially responding to relative humidity in the atmosphere. A moisture sensor having an electrolyte salt such as lithium chloride detects only humidity in a narrow range so that when it is allowed to stand in a high humidity atmosphere for a long period of time, the electrolyte salt therein is eluted or diluted resulting in deterioration of the moisture sensitive characteristic of the sensor, and accordingly it cannot be used for determination of high humidity. Also, a moisture sensor having a hygroscopic resin or the like, in which conductive particles or fibers are dispersed, cannot detect a humidity in a wide range because it exhibits a steep variation of the resistance thereof in a high humidity atmosphere, while it is not sensitive to low humidity.

On the other hand, a moisture sensor having, as a moisture sensitive film, a hydrophilic polymer film or a polyhydrolyte has been put into practical use because it is advantageous over the above-discussed sensors in that it is easily produced; it has excellent reproducibility and interchangeability; it operates in a wide moisture sensitive range; it has a high sensitivity due to wide variation of the resistance; and it responds rapidly. This moisture sensitive film is formed on a substrate by the use of a dipping technique, a spin casting method, or the like, in general. However, these techniques do not provide a moisture sensitive film of the desired pattern on the substrate. Also, a moisture sensitive polymer film formed by a wet etching technique using an etchant has a water resistance and a solvent resistance due to cross-linkage/polymerization and/or heat treatment employed by the etching process, so that a wet etching technique cannot be applied to the moisture sensitive polymer film. Thus, the moisture sensitive polymer film is usually formed into a pattern in such a manner that the portion of the polymer film to be connected to the lead wire is melted out by means of a soldering tool, or removed together with a masking tape which was placed on the substrate prior to the formation of the polymer film. These methods are undesirable as the moisture sensitive polymer film deteriorates and/or blisters at the edge portions due to the heat of the soldering tool. Moreover, these methods do not provide a compact, accurate and reproducible pattern; for instance, a pattern having a size of 1 mm or less is not obtainable.

Although a screen printing method is known as another pattern formation technique, it requires a polymer solution having a high viscosity which tends to change, resulting in nonuniform quality, and also cannot provide an accurate and reproducible pattern thereby making the formation of a highly fine pattern difficult. For these reasons, a screen printing method is not usually used for the formation of a moisture sensitive polymer film.

As described above, it is difficult to form a fine and accurately patterned moisture sensitive polymer film by the use of the conventional techniques, so that a moisture sensor having a fine and accurately patterned moisture sensitive polymer film has not yet been developed.

A technology to miniaturize moisture sensors and to compound a plurality of moisture sensors has recently been developed, and a field effect transistor (FET) moisture sensor in which a moisture sensor material is disposed on a gate of FET has been developed. Thus, a technology to form a moisture sensitive film having a fine and accurate pattern has become increasingly required.

SUMMARY OF THE INVENTION

The method for production of a moisture sensor which overcomes the above-discussed disadvantages of the prior art, comprises forming a moisture sensitive polymer film on a substrate, disposing a patterned masking material on said moisture sensitive polymer film, and etching said moisture sensitive film by means of an oxygen plasma.

The moisture sensitive polymer film is subjected to a heat treatment prior to said etching step.

The moisture sensitive polymer film is heat-treated at a temperature ranging from 150° C. to 250° C.

The moisture sensitive polymer film is made of at least one selected from the group consisiting of cellulose, polyamide, polyacrylate, polystyrenesulfonate, and polyvinyl alcohol.

Thus, the invention described herein makes possible the objects of providing a method for the production of a moisture sensor wherein a desired fine pattern of the moisture sensitive film is formed with fair accuracy and reproducibility; providing a method for the production of a minimized moisture sensor; providing a method for the production of a moisture sensor which is suitable to a wafer treatment to make a number of sensor units on one substrate thereby reducing production cost; and providing a method for the production of a moisture sensor wherein the moisture sensitive film does not peel from the substrate at production, resulting in an improvement of the yield and reliability of the sensor.

BRIEF DESCRIPTION OF THE DRAWINGS

This invention may be better understood and its numerous objects and advantages will become apparent to those skilled in the art by reference to the accompanying drawings as follows.

DESCRIPTION OF THE INVENTION

Organic polymers consist mainly of carbon, hydrogen and oxygen linked in a straight chain or a ring. Upon subjecting the organic polymers to a high temperature in an oxygen atmosphere or an oxygen plasma, they are decomposed and/or oxidized to produce $CO_2$ and $H_2O$. It is known that a photoresist used in an etching process is eliminated by utilizing its decomposition and/or oxidation. The present invention was completed by the application of such a technique to moisture sensitive polymers.

The arrangement, function and effects of the invention will now be described with reference to the drawings showing embodiments of the invention. The following illustrates the most typical examples, but it is to be understood that these are not intended to limit the scope of the invention and that changes and modifications thereof are within the technical scope of the invention.

FIGS. 1(A) to (E) illustrate a manufacturing process according to this invention.

Figure 1:
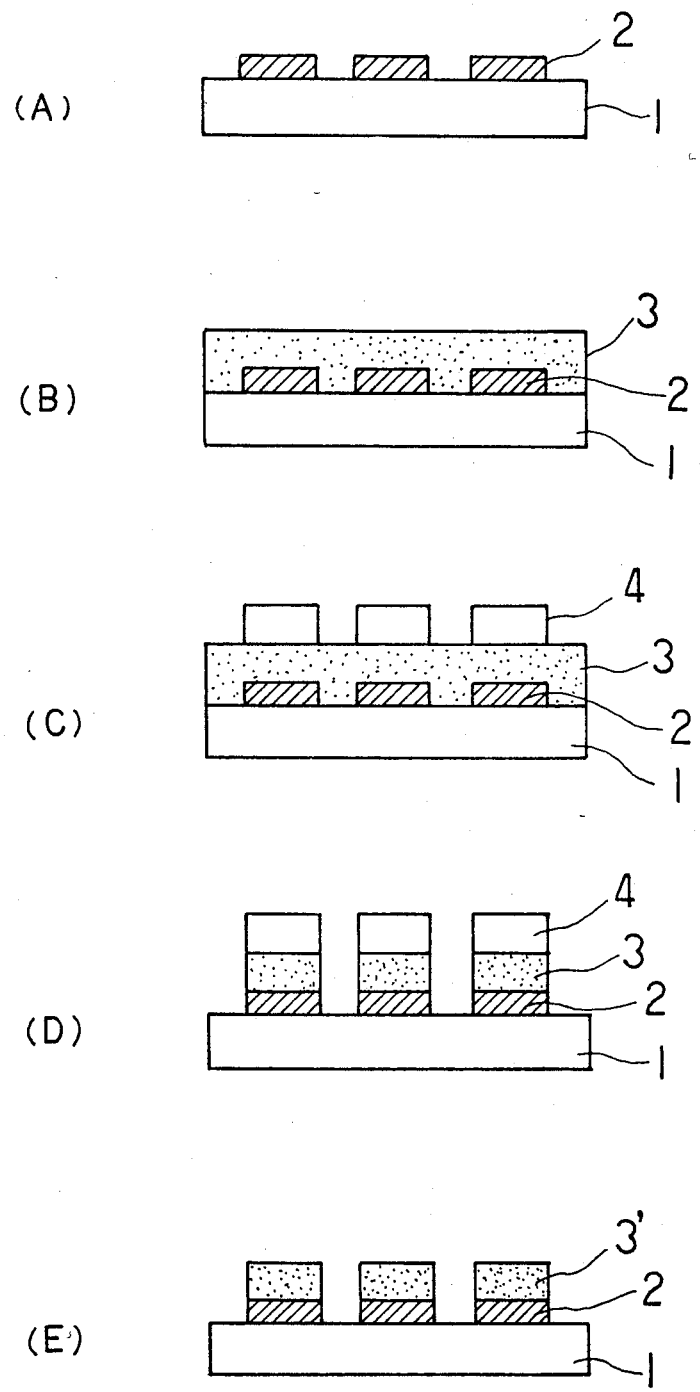
FIGS. 1(A) to (E) are partly sectional views illustrating a manufacturing process of a moisture sensor according to this invention.

As shown in FIG. 1(A), a number of electrodes 2 for detecting an impedance are disposed having a given pitch on a substrate 1 made of an insulator such as glass, alumina or the like, or a semiconductor such as silicone or the like. The dispositon pitch and the width of the electrodes 2 may be as small as about 1 mm or less. As a material of the electrodes 2, noble metals such as gold or platinum which are not oxidized within an oxygen plasma are preferably used.

Then, a polymer sulution is coated on the substrate 1 and the electrodes 2 by a dipping method or a spin casting method, as shown in FIG. 1(B), followed by heat treatment to produce cross-linkage/polymerization resulting in a thin polymer film 3. Examples of the polymer are cellulose, polyamide, polyacrylate, polystyrenesulfonate, polyvinyl alcohol or the like. Polyvinyl alcohol is preferably used due to its good moisture sensitive characteristic. The polymer is dissolved in a solvent such as water or a polyhydric alcohol to prepare the above-mentioned polymer solution.

Then, a resist such as a photo-resist is formed having the desired pattern on the thin polymer film 3 as shown in FIG. 1(C), followed by an exposure to an oxygen plasma to thereby etch the thin polymer film 3. Although the resist 4 is likewise etched when the thin polymer film 3 is etched, the resist 4 still remains on the thin polymer film 3, as shown in FIG. 1(D), when the uncovered portion of the film 3 has been removed because the thickness of the resist 4 is sufficiently greater than that of the polymer film 3. The resist 4 remaining on the thin polymer film 3 is removed, as shown in FIG. 1(E), by a releasing agent or a solvent thereby forming the moisture sensitive film 3' having a desired pattern which corresponds to the pattern of the resist 4. Examples of the resist are a resist made of a polymer such as vinyl acetate polymer or the like by the use of a printing method; a metal film prepared by a vacuum evaporation technique; a masking metal board; and a dry film resist, in addition to a well known photo-resist.

The etching process using an oxygen plasma has to be carried out in such a manner that the moisture sensitive film does not change its quality due to an increase in the temperature of the substrate. When, for example, the frequency output is reduced as much as possible and a pure oxygen gas is used as an etchant rather than a mixture of argon gas and oxygen gas or a mixture of nitrogen gas and oxygen gas, a considerable reduction of the time necessary to complete the etching process is attained thereby depressing an undesirable increase in the substrate temperature.

The resulting moisture sensor shown in FIG. 1(E) may be divided, if desired, into each unit including a moisture sensitive film 3' or each group including a plurality of units in a practical use.

Figure 4:
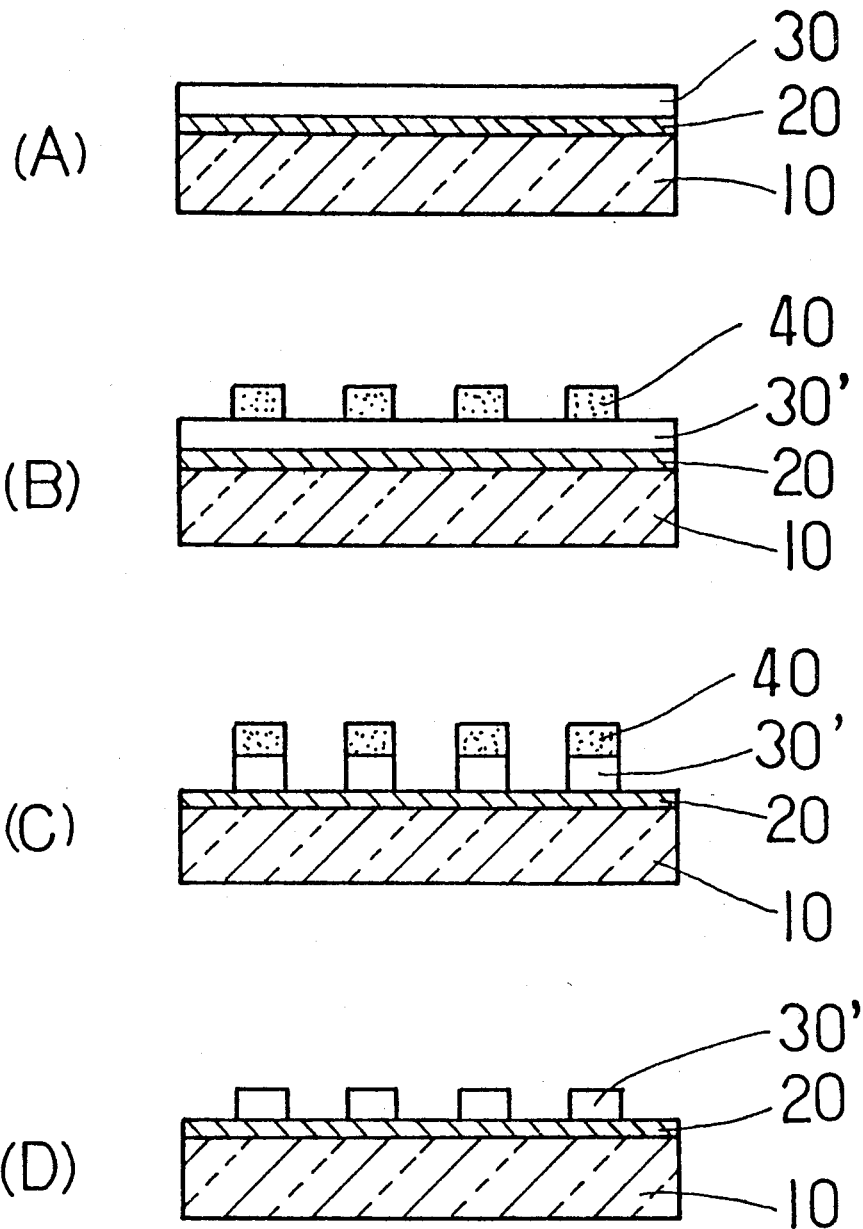
FIGS. 4(A) to (D) are partly sectional views illustrating another manufacturing process of a moisture sensor according to this invention.

FIGS. 4(A) to (D) show another manufacturing process according to this invention. As shown in FIG. 4(A), an electrode 20 made of a noble metal such as gold or platinum is desposed on a substrate 10 made of an insulator such as glass, alumina or the like, or a semiconductor made of silicone or the like. A moisture sensitive film 30 is formed on the substrate 10 having the electrode 20 thereon in the same manner as shown in FIG. 1(B). Such a moisture sensitive film 30 may be constituted by a plurality of films instead of a single one. As a material of the moisture sensitive film 30, the same polymers as the afore-mentioned film 3 may be used individually or plurally, if desired, mixed with additives. The formed thin film 30 is then subjected to a heat treatment to form a close moisture sensitive film 30' with an improved chemical bonding strength and moisture sensitive characteristic. For example, a moisture sensitive film 30 made of polyvinyl alcohol is heattreated at a temperature ranging from 150° C. to 250° C. for 10 to 30 minutes, resulting in an improved moisture sensitive film 30' which has a moisture sensitive characteristic exhibiting an improved linear relationship between the impedance and the relative humidity thereby allowing for an improvement of the determination accuracy and an improvement of the stability and reproducibility of the operation characteristic. The heat-treating temperature is set at 250° C. or lower, preferably 180° C. to 200° C., because when the temperature rises over 250° C., polyvinyl alcohol is vigorously decomposed.

EXAMPLE 1

Figure 2:
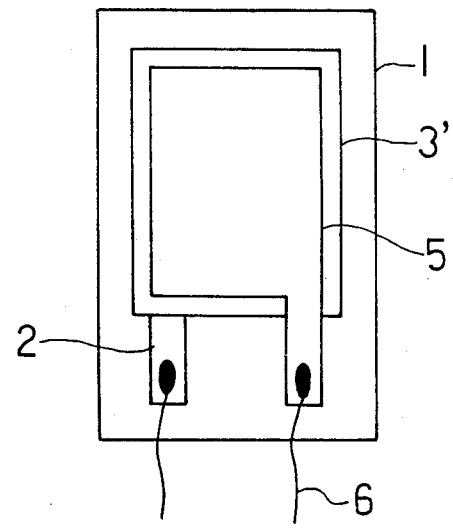
FIG. 2 is a plan view of a unit of a moisture sensor produced according to the process shown in FIG. 1.

According to the procedure shown in FIGS. 1(A) to (E), a number of bottom electrodes having a desired pattern are formed on a glass substrate by a masking evaporation technique. Polyvinyl alcohol powder is dissolved in water to prepare an aqueous solution of polyvinyl alcohol, which is then coated on the patterned electrodes by a spin casting method followed by a drying treatment and a heat treatment. On the resulting moisture sensitive polymer film a resist (for example, a dry film resist) is formed having a desired fine pattern, and then subjected to an oxygen plasma etching process, which is completed within about 20 minutes at a radio frequency output of 150 W under an oxygen pressure of 0.4 Torr using a cylindrical plasma etching apparatus which has a diameter of 250 mm and a length of 300 mm. Upon completion of the etching process, the remaining resist on the moisture sensitive polymer film is removed by a solvent such as acetone or methylene chloride. Thereafter, an upper electrode is formed as the postresist on the moisture sensitive film by a masking evaporation technique, resulting in the desired moisture sensor. A unit of the moisture sensor is shown in FIG. 2, wherein the bottom electrode 2 is formed on the glass substrate 1, the moisture sensitive film 3' is formed on the bottom electrode 2, further the upper electrode 5 is formed on the moisture sensitive film 3', and the extended edges of both electrodes are connected to a detecting circuit by lead wires 6 thereby allowing for the detection of a variation in the impedance depending upon humidity in the atmosphere, so that the humidity can be determined.

EXAMPLE 2

Figure 3:
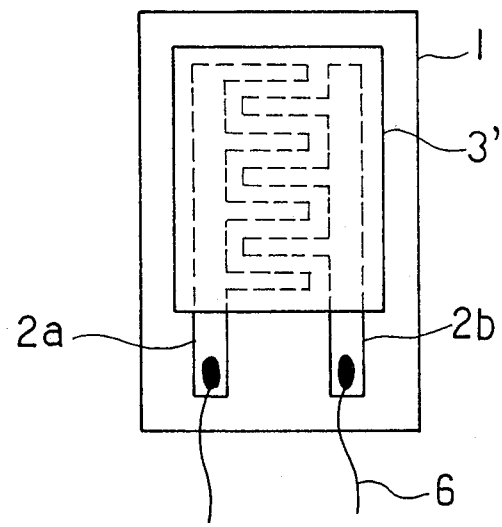
FIG. 3 is a plan view of a unit of another moisture sensor produced according to the process shown in FIG. 1.

A pair of comb-shaped electrode metal films are formed on a glass substrate by a photo-etching technique. Then, the formation of a moisture sensitive film and a resist is in turn conducted and an oxygen plasma etching process and the elimination process of the resist are further carried out, in the same manner as in Example 1, resulting in the desired moisture sensor unit as shown in FIG. 3 wherein a pair of comb-shaped electrodes 2a and 2b are formed on the glass substrate 1, and the moisture sensitive film 3' is formed on the electrodes 2a and 2b which are electrically connected to a detecting circuit by lead wires 6.

EXAMPLE 3

According to the procedure shown in FIGS. 4(A) to (D), a number of gold electrodes 20 are disposed on a glass substrate 10, on which an aqueous solution of polyvinyl alcohol is coated by a dipping technique or a spin casting method to form a moisture sensitive film 30 having a thickness of about 5 μm. The formed moisture sensitive film 30 is then heat treated at 180° C. to 200° C. for 10 to 30 minutes resulting in an improved moisture sensitive film 30', on which a patterned photo-resist 40 is formed.

Figure 5:
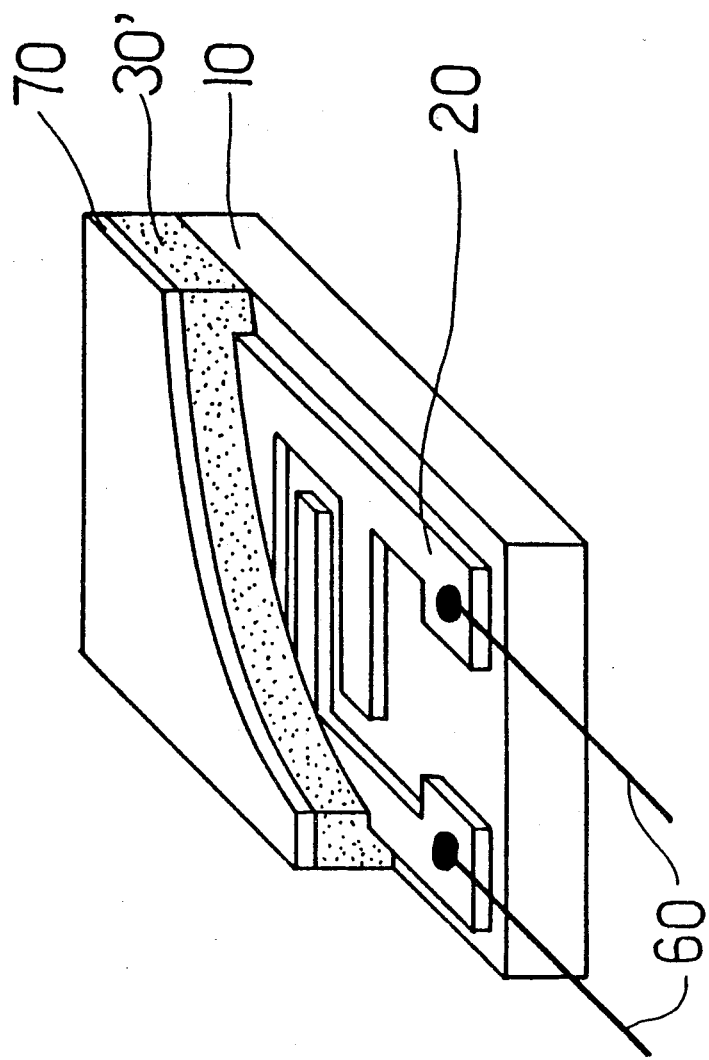
FIG. 5 is a partly perspective sectional view of a unit of the moisture sensor produced according to the process shown in FIG. 4.

The moisture sensitive film 30' is subjected to an oxygen plasma etching process in the same manner as in Example 1. The remaining resist 40 on the moisture sensitive film 30' is also removed in the same manner as in Example 1. The resulting moisture sensor is divided into units, if desired, as shown in FIG. 5, wherein on the glass substrate 10 a pair of comb-shaped electrodes 20 are disposed, on which the moisture sensitive film 30' is formed, the moisture sensitive film 30' being covered with a protector film 70, and the comb-electrodes 20 being electrically connected to a detecting circuit by lead wires 60.

Since the moisture sensitive film 30' is formed having a pattern with a pitch of 1 mm or smaller on the substrate 10, the resulting moisture sensor unit is effectively minimized.

It is understood that various other modification will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A method for production of a moisture sensor comprising forming a moisture sensitive polymer film on a substrate, disposing a patterned masking material on said moisture sensitive polymer film, and etching said moisture sensitive film by means of an oxygen plasma.

2. A method for preparation of a moisture sensor according to claim 1, wherein said moisture sensitive polymer film is subjected to a heat treatment prior to said etching step.

3. A method for production of a moisture sensor according to claim 2, wherein said moisture sensitive polymer film is heat-treated at a temperature ranging from 150° C. to 250° C.

4. A method for production of a moisture sensor according to claim 1, wherein said moisture sensitive polymer film is made of at least one selected from the group consisting of cellulose, polyamide, polyacrylate, polystyrenesulfonate, and polyvinyl alcohol.

5. A method for production of a moisture sensor according to claim 2, wherein said moisture sensitive polymer film is made of at least one selected from the group consisting of cellulose, polyamide, polyacrylate, polystyrenesulfonate, and polyvinyl alcohol.

6. A method for production of a moisture sensor according to claim 3, wherein said moisture sensitive polymer film is made of at least one selected from the group consisting of cellulose, polyamide, polyacrylate, polystyrenesulfonate, and polyvinyl alcohol.

* * * * *